United States Patent
Cheng et al.

(10) Patent No.: US 11,734,818 B2
(45) Date of Patent: Aug. 22, 2023

(54) MODEL, DIAGNOSTIC METHOD, AND APPLICATION THEREOF

(71) Applicant: LISEN IMPRINTING DIAGNOSTICS, INC., Dover, DE (US)

(72) Inventors: Tong Cheng, Jiangsu (CN); Ning Zhou, Jiangsu (CN)

(73) Assignee: LISEN IMPRINTING DIAGNOSTICS WUXI CO., LTD, Wuxi (CN)

(*) Notice: Subject to any disclaimer, the term of this patent is extended or adjusted under 35 U.S.C. 154(b) by 799 days.

(21) Appl. No.: 16/615,755

(22) PCT Filed: May 21, 2018

(86) PCT No.: PCT/CN2018/087661
§ 371 (c)(1),
(2) Date: Apr. 27, 2020

(87) PCT Pub. No.: WO2018/214845
PCT Pub. Date: Nov. 29, 2018

(65) Prior Publication Data
US 2020/0255890 A1    Aug. 13, 2020

(30) Foreign Application Priority Data

May 22, 2017 (CN) .......................... 201710363711.9
May 16, 2018 (CN) .......................... 201810468315.7

(51) Int. Cl.
*G06T 7/00* (2017.01)
*G16B 5/00* (2019.01)
(Continued)

(52) U.S. Cl.
CPC .......... *G06T 7/0012* (2013.01); *C12Q 1/6886* (2013.01); *G16B 5/00* (2019.02);
(Continued)

(58) Field of Classification Search
CPC ......... G06T 7/0012; G06T 2207/10056; G06T 2207/30096; C12Q 1/6886; C12Q 1/6841;
(Continued)

(56) References Cited

U.S. PATENT DOCUMENTS

| 6,235,474 B1 | 5/2001 | Feinberg |
| 2002/0045257 A1 | 4/2002 | Feinberg et al. |

(Continued)

FOREIGN PATENT DOCUMENTS

| CA | 2729554 A1 * | 12/2009 | ........... C12Q 1/6809 |
| JP | 2001507703 A | 6/2001 | |

(Continued)

OTHER PUBLICATIONS

Ribarska et al., Specific changes in the expression of imprinted genes in prostate cancer, 2012, Asian J. of Andrology: 14, 436-450. (Year: 2012).*

(Continued)

*Primary Examiner* — Matthew C Bella
*Assistant Examiner* — Kathleen M Broughton
(74) *Attorney, Agent, or Firm* — Yong Chen; Lin Sun-Hoffman; Liu Chen & Hoffman LLP

(57) ABSTRACT

A model and an application thereof, the model being used for detecting a benign and malignant degree of a tumor. The model grades a change of an imprinted gene in a tumor by calculating a deletion expression quantity of the imprinted gene and a copy number abnormal expression quantity of the imprinted gene. The detection model and device in the present invention presents the expression of loss of imprinting in a sample of a tumor patient in a direct way for the first time; based on an imprinted gene in situ labeling method, a change of an imprinted gene is detected objectively, directly, (Continued)

early, and precisely, and a quantitative model can be provided, to make a great contribution to molecular pathology diagnosis.

20 Claims, 6 Drawing Sheets

(51) Int. Cl.
    G16B 25/10      (2019.01)
    C12Q 1/6886    (2018.01)
    G16H 50/20     (2018.01)
    C12Q 1/6841    (2018.01)

(52) U.S. Cl.
    CPC ........... *G16B 25/10* (2019.02); *C12Q 1/6841* (2013.01); *G06T 2207/10056* (2013.01); *G06T 2207/30096* (2013.01); *G16H 50/20* (2018.01)

(58) Field of Classification Search
    CPC .......... G16B 5/00; G16B 25/10; G16B 40/20; G16H 50/20
    See application file for complete search history.

(56) References Cited

U.S. PATENT DOCUMENTS

| | | | | |
|---|---|---|---|---|
| 2008/0274457 | A1* | 11/2008 | Eng | C12Q 1/6886 435/6.16 |
| 2010/0129874 | A1* | 5/2010 | Mitra | C12P 19/34 435/91.2 |
| 2012/0071343 | A1* | 3/2012 | Ma | C12Q 1/6886 435/6.12 |
| 2013/0209446 | A1 | 8/2013 | Shaughnessy, Jr. et al. | |
| 2014/0024032 | A1* | 1/2014 | Raj | C12Q 1/6841 435/6.11 |

FOREIGN PATENT DOCUMENTS

| | | | | |
|---|---|---|---|---|
| JP | 2003534005 | A | | 11/2003 |
| JP | 2009072197 | A | * | 4/2009 ............. A61K 31/00 |
| JP | 2014512172 | A | * | 5/2014 ........... C12Q 1/6809 |
| WO | WO-199829108 | A2 | | 7/1998 |

OTHER PUBLICATIONS

Barrow et al., Aberrant methylation of imprinted genes associated with invasive breast cancer, 2015, Int. J. Cancer: 137, 537-547. (Year: 2015).*
Extended European Search Report for Application No. 18806916.5, dated Feb. 11, 2021.
Qing Zhong et al., "Image-based computational quantification and visualization of genetic alterations and tumour heterogeneity," *Scientific Reports*, vol. 6, No. 1, pp. 1-12 (2016).
Fredrik Enlund et al., "Molecular analyses of the candidate tumor suppressor gene, *PLAGL1*, in benign and malignant salivary gland tumors," *European Journal of Oral Sciences*, vol. 112, No. 6, pp. 545-547 (2004).
F. Lin et al., "Evaluation of the Expression and Role of IGF Pathway Biomarkers in Human Sarcomas," *International Journal of Immunopathology and Pharmacology*, vol. 26, No. 1, pp. 169-177 (2013).
Jan Ahlen et al., "Insulin-Like Growth Factor Type 1 Receptor Expression Correlates to Good Prognosis in Highly Malignant Soft Tissue Sarcoma," *Clinical Cancer Research*, vol. 11, No. 1, pp. 206-216 (2005).
Kazuhiro Tsuji et al., "PEG10 is a probable target for the amplification at 7q21 detected in hepatocellular carcinoma," *Cancer Genetics and Cytogenetics*, vol. 198, pp. 118-125 (2010).
Kimberly J. Bussey et al., "*SNRPN* Methylation Patterns in Germ Cell Tumors as a Reflection of Primordial Germ Cell Development," *Genes, Chromosomes & Cancer*, vol. 32, pp. 342-352 (2001).

Annemarie Greife et al., "Concomitant downregulation of the imprinted genes DLK1 and MEG3 at 14q32.2 by epigenetic mechanisms in urothelial carcinoma," *Clinical Epigenetics*, vol. 6, No. 29, pp. 1-13 (2014).
Arnoud Boot et al., "Imprinted survival genes preclude loss of heterozygosity of chromosome 7 in cancer cells," *Journal of Pathology*, vol. 240, pp. 72-83 (2016).
Teodora Ribarska et al., "Specific changes in the expression of imprinted genes in prostate cancer—implications for cancer progression and epigenetic regulation," *Asian Journal of Andrology*, vol. 14, pp. 436-450 (2012).
Leonidas Benetatos et al., "MEG3 imprinted gene contribution in tumorigenesis," *International Journal of Cancer*, vol. 129, pp. 773-779 (2011).
Office Action in corresponding Japanese Application No. 2020-514319, dated Jan. 12, 2021.
International Search Report for Application No. PCT/CN2018/087661, dated Jul. 26, 2018.
Fay Wang et al., "A Novel in Situ RNA Analysis Platform for Formalin-Fixed, Paraffin-Embedded Tissues," *The Journal of Molecular Diagnostics*, vol. 14, No. 1, pp. 22-29, Jan. 2012.
Waki Hosoda et al., "GNAS mutation is a frequent event in pancreatic intraductal papillary mucinous neoplasms and associated adenocarcinomas," *Virchows Arch*, Jun. 2015.
Callum Livingstone, "IGF2 and cancer," *Endocrine-Related Cancer*, 20:6, pp. R321-R339, Oct. 2013.
Xinzhou Deng et al., "PEG10 plays a crucial role in human lung cancer proliferation, progression, prognosis and metastasis," *Oncology Reports*, pp. 2159-2167, 2014.
Zhennan Tian et al., "IGF2R Expression is Associated with the Chemotherapy Response and Prognosis of Patients with Advanced NSCLC," *Cellular Physiology and Biochemistry*, pp. 1578-1588, Oct. 2014.
Yasutomi Kamei et al., "Peg1/Mest in obese adipose tissue is expressed from the paternal allele in an isoform-specific manner," *FEBS Letters*, pp. 91-96, Dec. 2006.
Sonata Jarmalaite et al., "Tumor suppresor gene ZAC/PLAGL1: altered expression and loss of the nonimprinted allele in pheochromocytomas," *Cancer Genetics*, pp. 398-404, Jul. 2011.
Frederic Brioude et al., "Mutations of the Imprinted CDKN1C Gene as a Cause of the Overgrowth Beckwith-Wiedemann Syndrome: Clinical Spectrum and Functional Characterization," *Human Mutation*, vol. 36, No. 9, pp. 894-902, Sep. 2015.
Atsushi Kasamatsu et al., "Decorin in human oral cancer: A promising predictive biomarker of S-1 neoadjuvant chemosensitivity," *Biochemical and Biophysical Research Communications*, vol. 457, pp. 71-76, Jan. 2015.
Nina Chi Sabins et al., "DLK1: A Novel Target for Immunotherapeutic Remodeling of the Tumor Blood Vasculature," *Molecular Therapy*, vol. 21, No. 10, pp. 1958-1968, Oct. 2013.
Dorothee Pflueger et al., "Functional characterization of BC039389-GATM and KLK4-KRSP1 chimeric read-through transcripts which are up-regulated in renal cell cancer," *BMC Genomics*, vol. 16, pp. 1-14, Mar. 2015.
Rana Mroue et al., "Monoallelic Loss of the Imprinted Gene Grb10 Promotes Tumor Formation in Irradiated Nf1+/− Mice," *PLOS Genetics*, pp. 1-25, Jun. 2015.
Monica D. Nye et al., "Associations between Methylation of Paternally Expressed Gene 3 (PEG3), Cervical Intraepithelial Neoplasia and Invasive Cervical Cancer," *PLOS One*, vol. 8, Issue 2, e56325, Feb. 2013.
Jorge L. Sepulveda et al., High-defnition CpG methylation of novel genes in gastric carcinogenesis identified by next-generation sequencing, *Modern Pathology*, vol. 29, pp. 182-193, Feb. 2016.
Shin Yup Lee et al., "Polymorphisms in cancer-related pathway genes and lung cancer," *Eur Respir J.*, Oct. 2016.
Timothy M. Barrow et al., "Aberrant methylation of imprinted genes is associated with negative hormone receptor status in invasive breast cancer," *Int J Cancer.*, 137(3), pp. 537-547, Aug. 2015.

* cited by examiner (a)           (b)

(a)           (b)

MODEL, DIAGNOSTIC METHOD, AND APPLICATION THEREOF

CROSS-REFERENCE TO RELATED APPLICATIONS

This application is the national phase of International Application No. PCT/CN2018/087661, titled with "MODEL, DIAGNOSTIC METHOD, AND APPLICATION THEREOF", which claims the priority of Chinese Patent Application No. 201710363711.9, filed on May 22, 2017 and Chinese Patent Application No. 201810468315.7, filed on May 16, 2018, and the disclosures of which are hereby incorporated by reference.

FIELD

The present invention relates to the field of biotechnology, such as the field of genetic diagnosis, specifically to a model and diagnostic method and uses thereof.

BACKGROUND

According to international statistics on cancer, there are more than 8 million people who die of cancer every year worldwide. Therefore, early detection, diagnosis and treatment of cancer are particularly important. At the cellular level, cancer is produced by complex genetic and epigenetic changes that accumulate over time, ultimately leading to uncontrolled cell division.

Traditional pathology diagnosis for benign and malignant cells is based on cell size, morphology, invasiveness and their relationship to surrounding cellular tissues. The methods have great limitations on the early detection of cancer, so the cancer diagnosis method at the cellular and molecular level has once become a research hotspot.

At present, the determination of benign and malignant cancer and the determination of cancer type or cancer stage are largely depend on the morphology of the cells observed by histopathological sections stained with hematoxylin and eosin. However, this method has its inherent limitations. First, the method cannot observe changes in the molecular level at the time of tumorigenesis, while molecular changes can provide a more accurate basis for pre-diagnosis and diagnosis. Secondly, the diagnosis of cell morphology is a subjective judgment, which in itself will cause inaccurate diagnosis; the error caused by such subjective judgment has a great impact on the diagnosis of early cancer, especially the sensitivity and accuracy of early diagnosis of cancer is critical for patients. Finally, some malignant tumor cells have little difference from benign tumor cells in morphology.

From the perspective of genetics, the development of tumors is a multi-gene process. Epigenetic modification has great impact for the occurrence, diagnosis and treatment of tumors, and has also been applied clinically. A large number of scientific studies have confirmed the correlation between re-expression of imprinted genes and cell carcinogenesis.

Genomic imprinting is a way of epigenetic gene regulation, expressed as that for a particular gene, only allele from a particular parent can be expressed, while another allele appears as a silent gene.

SUMMARY

The present disclosure provides a model and diagnostic method and uses thereof.

The present disclosure provides a model, which is a model for grading an imprinted gene, comprising calculating the changes of total expression of an imprinted gene, of the expression of an imprinted gene with loss of imprinting, and of the expression of an imprinted gene with copy number variation in a tumor, to grade the expression of the imprinted gene.

Loss of imprinting refers to the activation (demethylation) of the allele in the imprinted gene that is previously silent, which is the most common and earliest epigenetic change in cancer, and this characteristic can be used as a pathological marker. In contrast, in healthy cells, the occurrence of imprinted gene with loss of imprinting is very low.

For an imprinted gene with loss of imprinting, after performing hematoxylin staining on a cell, there are two red/brown marks in the nucleus of the cell. For an imprinted gene with copy number variation, after performing hematoxylin staining on a cell, there are more than two red/brown markers in the nucleus of the cell. The copy number variation is caused by abnormal gene duplication in cancer cells, resulting in the expression of this gene as a triploid or even higher polyploid.

The mark after hematoxylin staining is, but not limited to, red or brown, and the marks after other staining method with other colors can also be used for calculating the expression of an imprinted gene, the expression of an imprinted gene with loss of imprinting and the expression of an imprinted gene with copy number variation.

In one embodiment of the present disclosure, the imprinted genes include Z1 to Z16, and wherein the imprinted gene Z1 is Gnas, the imprinted gene Z2 is Igf2, the imprinted gene Z3 is Peg10, the imprinted gene Z4 is Igf2r, the imprinted gene Z5 is Mest, the imprinted gene Z6 is Plagl1, the imprinted gene Z7 is Cdkn1c, the imprinted gene Z8 is Dcn, the imprinted gene Z9 is Dlk1, the imprinted gene Z10 is Gatm, the imprinted gene Z11 is Grb10, the imprinted gene Z12 is Peg3, the imprinted gene Z13 is Sgce, the imprinted gene Z14 is Slc38a4, the imprinted gene Z15 is Diras3, and the imprinted gene Z16 is Snrpn/Snurf.

In one embodiment of the present disclosure, the calculation of the imprinted gene expression comprises calculating the expression of combined imprinted genes, and wherein the combined imprinted genes are a combination of the 16 imprinted genes Z1 to Z16.

In some embodiments of the present disclosure, by calculating the loss of imprinting (LOI), copy number variation (CNV) and total expression (TE) of the imprinted Z2, the detection sensitivity for thyroid cancer can reach 71.4%; by calculating the loss of imprinting (LOI), copy number variation (CNV) and total expression (TE) of the imprinted Z3, the detection sensitivity for thyroid cancer can reach 78.6%; by calculating the loss of imprinting (LOI), copy number variation (CNV) and total expression (TE) of the imprinted Z4, the detection sensitivity for thyroid cancer can reach 78.6%; by calculating the loss of imprinting (LOI), copy number variation (CNV) and total expression (TE) of the imprinted Z5, the detection sensitivity for thyroid cancer can reach 64.3%; by calculating the loss of imprinting (LOI), copy number variation (CNV) and total expression (TE) of the imprinted Z6, the detection sensitivity for thyroid cancer can reach 57.1%; by calculating the loss of imprinting (LOI), copy number variation (CNV) and total expression (TE) of the imprinted Z8, the detection sensitivity for thyroid cancer can reach 58.3%; by calculating the loss of imprinting (LOI), copy number variation (CNV) and total expression (TE) of the imprinted Z9, the detection sensitivity for thyroid cancer can reach 64.3%; by calculating the loss of imprinting (LOI), copy number variation (CNV) and total expression (TE) of the imprinted Z10, the detection sensitivity for thyroid cancer can reach 71.4%; by calculating the loss of imprinting (LOI), copy number variation (CNV) and total expression (TE) of the imprinted Z11, the detection sensitivity for thyroid cancer can reach 71.4%; and by calculating the loss of imprinting (LOI), copy number variation (CNV) and total expression (TE) of the imprinted Z12, the detection sensitivity for thyroid cancer can reach 69.2%.

In some embodiments of the present disclosure, by calculating the loss of imprinting (LOI), copy number variation (CNV) and total expression (TE) of two or more than two imprinted genes, the detection sensitivity may be further increased. In a specific example, when an imprinted gene combination of two imprinted genes is detected, the detection sensitivity for thyroid cancer can reach 92.9% or more. For example, when a combination of Z3 and Z4 is detected, the detection sensitivity for thyroid cancer can reach 92.9% or more; when a combination of Z3 and Z10 is detected, the detection sensitivity for thyroid cancer can reach 92.9% or more; and when a combination of Z4 and Z9 is detected, the detection sensitivity for thyroid cancer can reach 92.9% or more.

In one embodiment of the present disclosure, the total expression of an imprinted gene, the expression of an imprinted gene with loss of imprinting and the expression of an imprinted gene with copy number variation are calculated by the following formulas:

Total expression of an imprinted gene=$(b+c+d)/(a+b+c+d) \times 100\%$;

Expression of a normal imprinted gene=$b/(b+c+d) \times 100\%$;

Expression of an imprinted gene with loss of imprinting=$c/(b+c+d) \times 100\%$;

Expression of an imprinting gene with copy number variation=$d/(b+c+d) \times 100\%$;

wherein, a represents that after performing hematoxylin staining on a cell, there is no mark in the nucleus of the cell, the imprinted gene has no expression; b represents that after performing hematoxylin staining on a cell, there is one red/brown mark in the nucleus of the cell, the imprinted gene exists; c represents that after performing hematoxylin staining on a cell, there are two red/brown marks in the nucleus of the cell, the imprinted gene loses imprinting; and d represents that after performing hematoxylin staining on a cell, there are more than two red/brown markers in the nucleus of the cell, the imprinted gene has an copy number variation.

In one embodiment of the present disclosure, the total expression of an imprinted gene, the expression of an imprinted gene with loss of imprinting and the expression of an imprinting gene with copy number variation are classified into 5 grades according to the total expression of an imprinted gene, the expression of an imprinted gene with loss of imprinting and the expression of an imprinting gene with copy number variation of the 16 imprinted genes Z1 to Z16, and the expression is based on the counting of at least 1,200 cells in the area with clear marks on a sample for each probe.

In one embodiment of the present disclosure, the expression of Z1 with loss of imprinting and the expression of Z1 with copy number variation are classified into 5 grades:

Grade 0: the expression of Z1 with loss of imprinting is less than 15% and/or the expression of Z1 with copy number variation is less than 1.5%;

Grade I: the expression of Z1 with loss of imprinting is 15-25% and/or the expression of Z1 with copy number variation is 1.5-2.5%;

Grade II: the expression of Z1 with loss of imprinting is 25-30% and/or the expression of Z1 with copy number variation is 2.5-4%;

Grade III: the expression of Z1 with loss of imprinting is 30-35% and/or the expression of Z1 with copy number variation is 4-6%; and Grade IV: the expression of Z1 with loss of imprinting is more than 35% and/or the expression of Z1 with copy number variation is more than 6%.

In one embodiment of the present disclosure, the expression of Z2 or Z12 with loss of imprinting and the expression of Z2 or Z12 with copy number variation are classified into 5 grades:

Grade 0: the expression of Z2 or Z12 with loss of imprinting is less than 15% and/or the expression of Z2 or Z12 with copy number variation is less than 1%;

Grade I: the expression of Z2 or Z12 with loss of imprinting is 15-20% and/or the expression of Z2 or Z12 with copy number variation is 1-2%;

Grade II: the expression of Z2 or Z12 with loss of imprinting is 20-25% and/or the expression of Z2 or Z12 with copy number variation is 2-3%;

Grade III: the expression of Z2 or Z12 with loss of imprinting is 25-35% and/or the expression of Z2 or Z12 with copy number variation is 3-5%; and Grade IV: the expression of Z2 or Z12 with loss of imprinting is more than 35% and/or the expression of Z2 or Z12 with copy number variation is more than 5%; and in the present disclosure, the expression of an imprinted gene with loss of imprinting and the expression of an imprinting gene with copy number variation for Z2 and Z12 are independent to each other.

In one embodiment of the present disclosure, the expression of Z3, Z4, Z9, Z10 or Z11 with loss of imprinting and the expression of Z3, Z4, Z9, Z10 or Z11 with copy number variation are classified into 5 grades:

Grade 0: the expression of Z3, Z4, Z9, Z10 or Z11 with loss of imprinting is less than 15% and/or the expression of Z3, Z4, Z9, Z10 or Z11 with copy number variation is less than 1%;

Grade I: the expression of Z3, Z4, Z9, Z10 or Z11 with loss of imprinting is 15-20% and/or the expression of Z3, Z4, Z9, Z10 or Z11 with copy number variation is 1-2.5%;

Grade II: the expression of Z3, Z4, Z9, Z10 or Z11 with loss of imprinting is 20-30% and/or the expression of Z3, Z4, Z9, Z10 or Z11 with copy number variation is 2.5-4%;

Grade III: the expression of Z3, Z4, Z9, Z10 or Z11 with loss of imprinting is 30-35% and/or the expression of Z3, Z4, Z9, Z10 or Z11 with copy number variation is 4-6%; and Grade IV: the expression of Z3, Z4, Z9, Z10 or Z11 with loss of imprinting is more than 35% and/or the expression of Z3, Z4, Z9, Z10 or Z11 with copy number variation is more than 6%; and in the present disclosure, the expression of an imprinted gene with loss of imprinting and the expression of an imprinting gene with copy number variation for Z3, Z4, Z9, Z10 and Z11 are independent to each other.

In one embodiment of the present disclosure, the expression of Z5, Z6, Z8, Z13 or Z16 with loss of imprinting and the expression of Z5, Z6, Z8, Z13 or Z16 with copy number variation are classified into 5 grades:

Grade 0: the expression of Z5, Z6, Z8, Z13 or Z16 with loss of imprinting is less than 15% and/or the expression of Z5, Z6, Z8, Z13 or Z16 with copy number variation is less than 1%;

Grade I: the expression of Z5, Z6, Z8, Z13 or Z16 with loss of imprinting is 15-20% and/or the expression of Z5, Z6, Z8, Z13 or Z16 with copy number variation is 1-2.5%;

Grade II: the expression of Z5, Z6, Z8, Z13 or Z16 with loss of imprinting is 20-25% and/or the expression of Z5, Z6, Z8, Z13 or Z16 with copy number variation is 2.5-4%;

Grade III: the expression of Z5, Z6, Z8, Z13 or Z16 with loss of imprinting is 25-35% and/or the expression of Z5, Z6, Z8, Z13 or Z16 with copy number variation is 4-6%; and Grade IV: the expression of Z5, Z6, Z8, Z13 or Z16 with loss of imprinting is more than 35% and/or the expression of Z5, Z6, Z8, Z13 or Z16 with copy number variation is more than 6%; and in the present disclosure, the expression of an imprinted gene with loss of imprinting and the expression of an imprinting gene with copy number variation for Z5, Z6, Z8, Z13 and Z16 are independent to each other.

In one embodiment of the present disclosure, the expression of Z7, Z14 or Z15 with loss of imprinting and the expression of Z7, Z14 or Z15 with copy number variation are classified into 5 grades:

Grade 0: the expression of Z7, Z14 or Z15 with loss of imprinting is less than 10% and/or the expression of Z7, Z14 or Z15 with copy number variation is less than 0.5%;

Grade I: the expression of Z7, Z14 or Z15 with loss of imprinting is 10-15% and/or the expression of Z7, Z14 or Z15 with copy number variation is 0.5-1%;

Grade II: the expression of Z7, Z14 or Z15 with loss of imprinting is 15-20% and/or the expression of Z7, Z14 or Z15 with copy number variation is 1-2%;

Grade III: the expression of Z7, Z14 or Z15 with loss of imprinting is 20-25% and/or the expression of Z7, Z14 or Z15 with copy number variation is 2-3%; and Grade IV: the expression of Z7, Z14 or Z15 with loss of imprinting is more than 25% and/or the expression of Z7, Z14 or Z15 with copy number variation is more than 3%; and in the present disclosure, the expression of an imprinted gene with loss of imprinting and the expression of an imprinting gene with copy number variation for Z7, Z14 and Z15 are independent to each other.

In one embodiment of the present disclosure, a device is provided, which comprises the following units:

(1) sample unit for obtaining a test sample;

(2) probe design unit for designing a probe specific for the sequence of an imprinted gene;

(3) detection unit for performing in situ hybridization of the probe of step (2) to the test sample;

(4) analysis unit for analyzing microscopic images and determining the expression level of the imprinted gene;

wherein, the analysis unit is operated by calculating the total expression of the imprinted gene, the expression of the imprinted gene with loss of imprinting and the expression of the imprinted gene with copy number variation, using the model, and grading the expression of the imprinted gene with loss of imprinting and the expression of the imprinted gene with copy number variation, to determine the benignity or malignancy of a tumor.

For an imprinted gene with loss of imprinting, after performing hematoxylin staining on a cell, there are two red/brown marks in the nucleus of the cell. For an imprinted gene with copy number variation, after performing hematoxylin staining on a cell, there are more than two red/brown markers in the nucleus of the cell. The copy number variation is caused by abnormal gene duplication in cancer cells, resulting in the expression of this gene as a triploid or even higher polyploid.

The mark after hematoxylin staining is, but not limited to, red or brown, and the marks after other staining method with other colors can also be used for calculating the total expression of an imprinted gene, the expression of an imprinted gene with loss of imprinting and the expression of an imprinted gene with copy number variation.

The device is used to visually detect the changes of imprinted genes in different types of tumors at single cell and at tissue levels in early stage, so as to determine a benign tumor or a malignant tumor in different stages, which provides the most favorable treatment opportunities for patients with early tumors.

In one embodiment of the present disclosure, the test sample of step (1) is human tissue and/or cells.

The test samples are feasible as long as the RNA is subjected to fixation in time. Those skilled in the art can select the treatment methods according to needs, which is not particularly limited here. The test samples described in the present disclosure include tissue paraffin sections, and/or cells from needle biopsy, and/or exfoliated cells obtained by natural exfoliation and mechanical methods.

In one embodiment of the present disclosure, the specific operation steps of the paraffin section of the tissue are as follows: obtaining a human tumor tissue sample, fixing the sample with 10% neutral buffered formalin or other fixation methods in time, embedding the sample into paraffin, cutting into a section with a thickness of 10 μm, and loading onto a positively charged slide as a tissue section. Because the section is only 10 μm thick, some of the nuclei are not intact under the microscope, so some false negative results maybe occur for imprinted gene with loss of imprinting.

In one embodiment of the present disclosure, other fixation methods include alcohol-based tissue fixation, and the specific steps of the alcohol-based tissue fixation are as follows: putting the test sample into the anti-corrosion fixing solution described in patent ZL200710024048.6, and fixing at room temperature for more than 24 hours.

The inventor found that different fixation methods will lead to different classification standards, and each index may fluctuate by 20%.

In one embodiment of the present disclosure, the specific operation steps of the needle biopsy for section are: obtaining human cells, and fixing them with 10% neutral buffered formalin or other fixation methods in time.

The specific operation steps for exfoliated cells obtained by natural exfoliation and mechanical methods are: obtaining human cells, and fixing them with 10% neutral buffered formalin or other fixation methods in time.

Because needle biopsy is less harmful to patients, the sampling process is simple, and the cells can be located, compared with the circulation characteristics of blood, needle biopsy has special advantages.

In one embodiment of the present disclosure, the test sample is cells from needle biopsy.

In one embodiment of the present disclosure, the imprinted genes include Z1 to Z16, and wherein the imprinted gene Z1 is Gnas, the imprinted gene Z2 is Igf2, the imprinted gene Z3 is Peg10, the imprinted gene Z4 is Igf2r, the imprinted gene Z5 is Mest, the imprinted gene Z6 is Plagl1, the imprinted gene Z7 is Cdkn1c, the imprinted gene Z8 is Dcn, the imprinted gene Z9 is Dlk1, the imprinted gene Z10 is Gatm, the imprinted gene Z11 is Grb10, the imprinted gene Z12 is Peg3, the imprinted gene Z13 is Sgce, the imprinted gene Z14 is Slc38a4, the imprinted gene Z15 is Diras3, and the imprinted gene Z16 is Snrpn/Snurf.

The imprinted genes Z1 (Gnas), Z2 (Igf2), Z3 (Peg10), Z4 (Igf2r), Z5 (Mest), Z6 (Plagl1), Z7 (Cdkn1c), Z8 (Dcn), Z9 (Dlk1), Z10 (Gatm), Z11 (Grb10), Z12 (Peg3), Z13 (Sgce), Z14 (Slc38a4), Z15 (Diras3) and Z16 (Snrpn/Snurf) are expressed to varying degrees in tumor tissues, and when a malignant lesion occurs, the expression level and imprinting status will change significantly.

In one embodiment of the present disclosure, the probes are designed according to the imprinted genes Z1-Z16, namely Gnas, Igf2, Peg10, Igf2r, Mest, Plagl1, Cdkn1c, Dcn, Dlk1, Gatm, Grb10, Peg3, Sgce, Slc38a4, Diras3 and Snrpn/Snurf. Specifically, a sequence within an intron of each gene is selected as a probe. The specific probes are designed by Advanced Cell Diagnostics.

In one embodiment of the present disclosure, the in situ hybridization is RNAscope in situ hybridization.

In one embodiment of the present disclosure, the RNAscope in situ hybridization is performed by using singleplex or multiplex color assay kit or singleplex or multiplex fluorescence assay kit, preferably singleplex red/brown color assay kit or multiplex fluorescence assay kit.

The multiplex color assay kit or multiplex fluorescence assay kit include two or more channels of color assay kit or fluorescence assay kit. The two channels color assay kit or multiple channels fluorescence assay kit can use two imprinted gene probes to detect the expression of an imprinted gene and another gene or even the expression of multiple imprinted genes and non-imprinted genes.

By in situ hybridization using a probe and hemotoxylin staining of the nucleus, the signal is amplified. Under a 40× or 60× microscope, the presence of imprinted gene, imprinted gene with loss of imprinting, or imprinted gene with copy number variation in each nucleus is determined. By calculating the total expression of an imprinted gene, the expression of an imprinted gene with loss of imprinting and the expression of an imprinting gene with copy number variation, the benignity or malignancy of a tumor is determined. Due to the thickness of the section is only 10 microns, about 20% of the nuclei seen under the microscope are not intact, that is, there is a possibility of false negative results.

In one embodiment of the present disclosure, the benignity or malignancy of the tumor to be determined is classified as benign tumor, malignant potential tumor, early malignant tumor, moderate malignant tumor, or advanced malignant tumor.

In one embodiment of the present disclosure, the tumor is determined as a benign tumor, if the expression of all the imprinted genes Z1, Z2, Z3, Z4, Z5, Z6, Z7, Z8, Z9, Z10, Z11, Z12, Z13, Z14, Z15 and Z16 with loss of imprinting and the expression of all the imprinted genes Z1, Z2, Z3, Z4, Z5, Z6, Z7, Z8, Z9, Z10, Z11, Z12, Z13, Z14, Z15 and Z16 with copy number variation is Grade 0; if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I; or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade I.

In one embodiment of the present disclosure, the tumor is determined as a malignant potential tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade I; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade II.

In one embodiment of the present disclosure, the tumor is determined as an early malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade II; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade III.

In one embodiment of the present disclosure, the tumor is determined as a moderate malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade III; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade IV, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade IV.

In one embodiment of the present disclosure, the tumor is determined as an advanced malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade IV; or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade IV.

In one embodiment of the present disclosure, the tumor is a conventional tumor in the art. In the present disclosure, the tumor is selected from, but not limited to, any one or a combination of at least two of thyroid tumors, lung tumors and brain tumors.

The present disclosure provides a detection method, comprising the steps of:

(1) obtaining a test sample;

(2) designing a probe specific for the sequence of an imprinted gene;

(3) performing in situ hybridization of the probe of step (2) to the test sample; and (4) analyzing microscopic images and determining the expression level of the imprinted gene;

by calculating the total expression of the imprinted gene, the expression of the imprinted gene with loss of imprinting and the expression of the imprinted gene with copy number variation, using the model, and grading the expression of the gene with loss of imprinting and the expression of the imprinted gene with copy number variation, to determine the benignity or malignancy of a tumor.

For an imprinted gene with loss of imprinting, after performing hematoxylin staining on a cell, there are two red/brown marks in the nucleus of the cell. For an imprinted gene with copy number variation, after performing hematoxylin staining on a cell, there are more than two red/brown markers in the nucleus of the cell. The copy number variation is caused by abnormal gene duplication in cancer cells, resulting in the expression of this gene as a triploid or even higher polyploid.

The mark after hematoxylin staining is, but not limited to, red or brown, and the marks after other staining method with other colors can also be used for calculating the expression of an imprinted gene, the expression of an imprinted gene with loss of imprinting and the expression of an imprinted gene with copy number variation.

The device is used to visually detect the changes of imprinted genes in different types of tumors at single cell and at tissue levels in early stage, so as to determine a benign tumor or a malignant tumor in different stage, which provides the most favorable treatment opportunities for patients with early tumors.

In one embodiment of the present disclosure, the test sample of step (1) is human tissue and/or cells.

The test samples are feasible as long as the RNA is subjected to fixation in time. Those skilled in the art can select the treatment methods according to needs, which is not particularly limited here. The test samples described in the present disclosure include tissue paraffin sections, and/or cells from needle biopsy, and/or exfoliated cells obtained by natural exfoliation and mechanical methods.

In one embodiment of the present disclosure, the specific operation steps of the paraffin section of the tissue are as follows: obtaining a human tumor tissue sample, fixing the sample with 10% neutral formalin or other fixation methods in time, embedding the sample into paraffin, cutting into a section with a thickness of 10 μm, and loading onto a positively charged slide as a tissue section. Because the section is only 10 μm thick, some of the nuclei are not intact under the microscope, so some false negative results maybe occur for imprinted gene with loss of imprinting.

In one embodiment of the present disclosure, other fixation methods include alcohol-based tissue fixation, and the specific steps of the alcohol-based tissue fixation are as follows: putting the test sample into the anti-corrosion fixing solution described in patent ZL200710024048.6, and fixing at room temperature for more than 24 hours.

The inventor found that different fixation methods will lead to different classification standards, and each index may fluctuate by 20%.

In one embodiment of the present disclosure, the specific operation steps of the needle biopsy for section are: obtaining human cells, and fixing them with 10% neutral buffered formalin or other fixation methods in time.

The specific operation steps for exfoliated cells obtained by natural exfoliation and mechanical methods are: obtaining human cells, and fixing them with 10% neutral buffered formalin or other fixation methods in time.

Because needle biopsy is less harmful to patients, the sampling process is simple, and the cells can be located, compared with the circulation characteristics of blood, needle biopsy has special advantages.

In one embodiment of the present disclosure, the test sample is cells from needle biopsy.

In one embodiment of the present disclosure, the imprinted genes include Z1 to Z16, and wherein the imprinted gene Z1 is Gnas, the imprinted gene Z2 is Igf2, the imprinted gene Z3 is Peg10, the imprinted gene Z4 is Igf2r, the imprinted gene Z5 is Mest, the imprinted gene Z6 is Plagl1, the imprinted gene Z7 is Cdkn1c, the imprinted gene Z8 is Dcn, the imprinted gene Z9 is Dlk1, the imprinted gene Z10 is Gatm, the imprinted gene Z11 is Grb10, the imprinted gene Z12 is Peg3, the imprinted gene Z13 is Sgce, the imprinted gene Z14 is Slc38a4, the imprinted gene Z15 is Diras3, and the imprinted gene Z16 is Snrpn/Snurf.

The imprinted genes Z1 (Gnas), Z2 (Igf2), Z3 (Peg10), Z4 (Igf2r), Z5 (Mest), Z6 (Plagl1), Z7 (Cdkn1c), Z8 (Dcn), Z9 (Dlk1), Z10 (Gatm), Z11 (Grb10), Z12 (Peg3), Z13 (Sgce), Z14 (Slc38a4), Z15 (Diras3) and Z16 (Snrpn/Snurf) are expressed to varying degrees in tumor tissues, and when a malignant lesion occurs, the expression level and imprinting status will change significantly.

In one embodiment of the present disclosure, the probes are designed according to the imprinted genes Z1-Z16, namely Gnas, Igf2, Peg10, Igf2r, Mest, Plagl1, Cdkn1c, Dcn, Dlk1, Gatm, Grb10, Peg3, Sgce, Slc38a4, Diras3 and Snrpn/Snurf. Specifically, a sequence within an intron of each gene is selected as a probe. The specific probes are designed by Advanced Cell Diagnostics.

In one embodiment of the present disclosure, the in situ hybridization is RNAscope in situ hybridization.

In one embodiment of the present disclosure, the RNAscope in situ hybridization is performed by using singleplex or multiplex color assay kit or singleplex or multiplex fluorescence assay kit, preferably singleplex red/brown color assay kit or multiplex fluorescence assay kit.

The multiplex color assay kit or multiplex fluorescence assay kit include two or more channels of color assay kit or fluorescence assay kit. The two channels color assay kit or multiple channels fluorescence assay kit can use two imprinted gene probes to detect the expression of an imprinted gene and another gene or even the expression of multiple imprinted genes and non-imprinted genes.

By in situ hybridization using a probe and hemotoxylin staining of the nucleus, the signal is amplified. Under a 40× or 60× microscope, the presence of imprinted gene, imprinted gene with loss of imprinting, or imprinted gene with copy number variation in each nucleus is determined. By calculating the expression of an imprinted gene, the expression of an imprinted gene with loss of imprinting and the expression of an imprinting gene with copy number variation, the benignity or malignancy of a tumor is determined. Due to the thickness of the section is only 10 microns, about 20% of the nuclei seen under the microscope are not intact, that is, there is a possibility of false negative results.

In one embodiment of the present disclosure, the expression of an imprinted gene with loss of imprinting and the expression of an imprinting gene with copy number variation are classified into 5 grades.

In one embodiment of the present disclosure, the 5 grades are classified according to the expression of an imprinted gene, the expression of an imprinted gene with loss of imprinting and the expression of an imprinting gene with copy number variation of the 16 imprinted genes Z1 to Z16, and the expression is based on the counting of at least 1,200 cells in the area with clear marks on a sample for each probe.

In one embodiment of the present disclosure, the expression of Z1 with loss of imprinting and the expression of Z1 with copy number variation are classified into 5 grades:

Grade 0: the expression of Z1 with loss of imprinting is less than 15% and/or the expression of Z1 with copy number variation is less than 1.5%;

Grade I: the expression of Z1 with loss of imprinting is 15-25% and/or the expression of Z1 with copy number variation is 1.5-2.5%;

Grade II: the expression of Z1 with loss of imprinting is 25-30% and/or the expression of Z1 with copy number variation is 2.5-4%;

Grade III: the expression of Z1 with loss of imprinting is 30-35% and/or the expression of Z1 with copy number variation is 4-6%; and Grade IV: the expression of Z1 with loss of imprinting is more than 35% and/or the expression of Z1 with copy number variation is more than 6%.

In one embodiment of the present disclosure, the expression of Z2 or Z12 with loss of imprinting and the expression of Z2 or Z12 with copy number variation are classified into 5 grades:

Grade 0: the expression of Z2 or Z12 with loss of imprinting is less than 15% and/or the expression of Z2 or Z12 with copy number variation is less than 1%;

Grade I: the expression of Z2 or Z12 with loss of imprinting is 15-20% and/or the expression of Z2 or Z12 with copy number variation is 1-2%;

Grade II: the expression of Z2 or Z12 with loss of imprinting is 20-25% and/or the expression of Z2 or Z12 with copy number variation is 2-3%;

Grade III: the expression of Z2 or Z12 with loss of imprinting is 25-35% and/or the expression of Z2 or Z12 with copy number variation is 3-5%; and Grade IV: the expression of Z2 or Z12 with loss of imprinting is more than 35% and/or the expression of Z2 or Z12 with copy number variation is more than 5%; and in the present disclosure, the expression of an imprinted gene with loss of imprinting and the expression of an imprinting gene with copy number variation for Z2 and Z12 are independent to each other.

In one embodiment of the present disclosure, the expression of Z3, Z4, Z9, Z10 or Z11 with loss of imprinting and the expression of Z3, Z4, Z9, Z10 or Z11 with copy number variation are classified into 5 grades:

Grade 0: the expression of Z3, Z4, Z9, Z10 or Z11 with loss of imprinting is less than 15% and/or the expression of Z3, Z4, Z9, Z10 or Z11 with copy number variation is less than 1%;

Grade I: the expression of Z3, Z4, Z9, Z10 or Z11 with loss of imprinting is 15-20% and/or the expression of Z3, Z4, Z9, Z10 or Z11 with copy number variation is 1-2.5%;

Grade II: the expression of Z3, Z4, Z9, Z10 or Z11 with loss of imprinting is 20-30% and/or the expression of Z3, Z4, Z9, Z10 or Z11 with copy number variation is 2.5-4%;

Grade III: the expression of Z3, Z4, Z9, Z10 or Z11 with loss of imprinting is 30-35% and/or the expression of Z3, Z4, Z9, Z10 or Z11 with copy number variation is 4-6%; and Grade IV: the expression of Z3, Z4, Z9, Z10 or Z11 with loss of imprinting is more than 35% and/or the expression of Z3, Z4, Z9, Z10 or Z11 with copy number variation is more than 6%; and in the present disclosure, the expression of an imprinted gene with loss of imprinting and the expression of an imprinting gene with copy number variation for Z3, Z4, Z9, Z10 and Z11 are independent to each other.

In one embodiment of the present disclosure, the expression of Z5, Z6, Z8, Z13 or Z16 with loss of imprinting and the expression of Z5, Z6, Z8, Z13 or Z16 with copy number variation are classified into 5 grades:

Grade 0: the expression of Z5, Z6, Z8, Z13 or Z16 with loss of imprinting is less than 15% and/or the expression of Z5, Z6, Z8, Z13 or Z16 with copy number variation is less than 1%;

Grade I: the expression of Z5, Z6, Z8, Z13 or Z16 with loss of imprinting is 15-20% and/or the expression of Z5, Z6, Z8, Z13 or Z16 with copy number variation is 1-2.5%;

Grade II: the expression of Z5, Z6, Z8, Z13 or Z16 with loss of imprinting is 20-25% and/or the expression of Z5, Z6, Z8, Z13 or Z16 with copy number variation is 2.5-4%;

Grade III: the expression of Z5, Z6, Z8, Z13 or Z16 with loss of imprinting is 25-35% and/or the expression of Z5, Z6, Z8, Z13 or Z16 with copy number variation is 4-6%; and Grade IV: the expression of Z5, Z6, Z8, Z13 or Z16 with loss of imprinting is more than 35% and/or the expression of Z5, Z6, Z8, Z13 or Z16 with copy number variation is more than 6%; and in the present disclosure, the expression of an imprinted gene with loss of imprinting and the expression of an imprinting gene with copy number variation for Z5, Z6, Z8, Z13 and Z16 are independent to each other.

In one embodiment of the present disclosure, the expression of Z7, Z14 or Z15 with loss of imprinting and the expression of Z7, Z14 or Z15 with copy number variation are classified into 5 grades:

Grade 0: the expression of Z7, Z14 or Z15 with loss of imprinting is less than 10% and/or the expression of Z7, Z14 or Z15 with copy number variation is less than 0.5%;

Grade I: the expression of Z7, Z14 or Z15 with loss of imprinting is 10-15% and/or the expression of Z7, Z14 or Z15 with copy number variation is 0.5-1%;

Grade II: the expression of Z7, Z14 or Z15 with loss of imprinting is 15-20% and/or the expression of Z7, Z14 or Z15 with copy number variation is 1-2%;

Grade III: the expression of Z7, Z14 or Z15 with loss of imprinting is 20-25% and/or the expression of Z7, Z14 or Z15 with copy number variation is 2-3%; and Grade IV: the expression of Z7, Z14 or Z15 with loss of imprinting is more than 25% and/or the expression of Z7, Z14 or Z15 with copy number variation is more than 3%; and in the present disclosure, the expression of an imprinted gene with loss of imprinting and the expression of an imprinting gene with copy number variation for Z7, Z14 and Z15 are independent to each other.

In one embodiment of the present disclosure, the benignity or malignancy of the tumor to be determined is classified as benign tumor, malignant potential tumor, early malignant tumor, moderate malignant tumor, or advanced malignant tumor.

In one embodiment of the present disclosure, the tumor is determined as a benign tumor, if the expression of all the imprinted genes Z1, Z2, Z3, Z4, Z5, Z6, Z7, Z8, Z9, Z10, Z11, Z12, Z13, Z14, Z15 and Z16 with loss of imprinting and the expression of all the imprinted genes Z1, Z2, Z3, Z4, Z5, Z6, Z7, Z8, Z9, Z10, Z11, Z12, Z13, Z14, Z15 and Z16 with copy number variation is Grade 0; if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I; or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade I.

In one embodiment of the present disclosure, the tumor is determined as a malignant potential tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade I; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade II.

In one embodiment of the present disclosure, the tumor is determined as an early malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade II; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade III.

In one embodiment of the present disclosure, the tumor is determined as a moderate malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade III; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade IV, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade IV.

In one embodiment of the present disclosure, the tumor is determined as an advanced malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade IV; or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade IV.

In some embodiments of the present disclosure, different tumors have different sensitivities to each imprinted gene, and each index of different tumors may fluctuate by 20%.

The present disclosure provides the model or the device for the manufacture of a medicament for determining and/or treating a tumor.

In one embodiment of the present disclosure, the tumor to be determined is classified as benign tumor, malignant potential tumor, early malignant tumor, moderate malignant tumor, or advanced malignant tumor.

In one embodiment of the present disclosure, the tumor is determined as a benign tumor, if the expression of all the imprinted genes Z1, Z2, Z3, Z4, Z5, Z6, Z7, Z8, Z9, Z10, Z11, Z12, Z13, Z14, Z15 and Z16 with loss of imprinting and the expression of all the imprinted genes Z1, Z2, Z3, Z4, Z5, Z6, Z7, Z8, Z9, Z10, Z11, Z12, Z13, Z14, Z15 and Z16 with copy number variation is Grade 0; if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I; or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade I.

In one embodiment of the present disclosure, the tumor is determined as a malignant potential tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade I; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade II.

In one embodiment of the present disclosure, the tumor is determined as an early malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade II; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade III.

In one embodiment of the present disclosure, the tumor is determined as a moderate malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade III; and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade IV, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade IV.

In one embodiment of the present disclosure, the tumor is determined as an advanced malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade IV; or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade IV.

Compared with prior art, the detection model and device of the present invention presents the expression of loss of imprinting in a sample of a tumor patient in a direct way for the first time; based on an imprinted gene in situ labeling method, a change of an imprinted gene is detected objectively, directly, early, and precisely, and a quantitative model can be provided, to make a great contribution to molecular pathology diagnosis.

After reading and understanding the accompanying drawings and detailed description, other aspects of the present disclosure will be understood.

BRIEF DESCRIPTION OF DRAWINGS

The drawings are used to provide a further understanding of the embodiments of the invention, and are to be construed as a part of the description of the invention.

FIG. 3(a) shows the expression of the 16 genes in a pathological section of Grade 0 thyroid tumor; FIG. 3(b) shows the expression of the 16 genes in a pathological section of Grade I thyroid tumor; FIG. 3(c) shows the expression of the 16 genes in a pathological section of Grade II thyroid tumor; FIG. 3(d) shows the expression of the 16 genes in a pathological section of Grade III thyroid tumor; and FIG. 3(e) shows the expression of the 16 genes in a pathological section of Grade IV thyroid tumor.

FIG. 4(a) shows the distribution range and grading standard of Z1 with loss of imprinting and Z1 with copy number variation in pathological sections of 17 thyroid tumors; FIG. 4(b) shows the distribution range and grading standard of Z2 with loss of imprinting and Z2 with copy number variation in pathological sections of 17 thyroid tumors; FIG. 4(c) shows the distribution range and grading standard of Z3 with loss of imprinting and Z3 with copy number variation in pathological sections of 17 thyroid tumors; FIG. 4(d) shows the distribution range and grading standard of Z4 with loss of imprinting and Z4 with copy number variation in pathological sections of 17 thyroid tumors;

FIG. 4(e) shows the distribution range and grading standard of Z5 with loss of imprinting and Z5 with copy number variation in pathological sections of 17 thyroid tumors; FIG. 4(f) shows the distribution range and grading standard of Z6 with loss of imprinting and Z6 with copy number variation in pathological sections of 17 thyroid tumors; FIG. 4(g) shows the distribution range and grading standard of Z8 with loss of imprinting and Z8 with copy number variation in pathological sections of 17 thyroid tumors; FIG. 4(h) shows the distribution range and grading standard of Z9 with loss of imprinting and Z9 with copy number variation in pathological sections of 17 thyroid tumors; FIG. 4(i) shows the distribution range and grading standard of Z10 with loss of imprinting and Z10 with copy number variation in pathological sections of 17 thyroid tumors; FIG. 4(j) shows the distribution range and grading standard of Z11 with loss of imprinting and Z11 with copy number variation in pathological sections of 17 thyroid tumors; FIG. 4(k) shows the distribution range and grading standard of Z12 with loss of imprinting and Z12 with copy number variation in pathological sections of 17 thyroid tumors; FIG. 4(l) shows the distribution range and grading standard of Z13 with loss of imprinting and Z13 with copy number variation in pathological sections of 17 thyroid tumors; and FIG. 4(m) shows the distribution range and grading standard of Z16 with loss of imprinting and Z16 with copy number variation in pathological sections of 17 thyroid tumors.

FIG. 5(a) shows the expression of the 16 genes in a section of black mole; and FIG. 5(b) shows the expression of the 16 genes in a section of skin malignant melanoma.

FIG. 6(a) shows the expression of the 16 genes in a section of benign lung tumor; and FIG. 6(b) shows the expression of the 16 genes in a section of lung cancer.

FIG. 7(a) shows the expression of the 16 genes in a section of benign bladder tumor; and FIG. 7(b) shows the expression of the 16 genes in a section of bladder cancer.

FIG. 7(a) shows the expression of the 16 genes in a section of benign pancreas tumor; and FIG. 7(b) shows the expression of the 16 genes in a section of pancreas cancer.

DETAILED DESCRIPTION

The examples herein will be described in detail below with reference to the drawings.

Genomic imprinting is a way of epigenetic gene regulation. For a particular gene, only allele from a particular parent can be expressed, while another allele appears as a silent gene.

The development of tumors is a multi-gene process. Epigenetic modification has great impact for the occurrence, diagnosis and treatment of tumors, and has also been applied clinically.

A large number of scientific studies have confirmed the correlation between re-expression of imprinted gene and cell carcinogenesis.

The present disclosure provides a detection method and device for directly diagnosing a loss of imprinting from a biopsy sample of a patient, and then determines whether the tumor is benign or malignant and the stage thereof before surgery, thereby providing a basis for surgery and precise treatment.

The present disclosure can accurately determine the type of tumor, fill the limitations of current tissue morphological diagnosis, enable early accurate diagnosis, and provide assistance for later targeted therapy.

The present disclosure is the first to detect the expression of imprinted genes at a single cell and tissue level, and allows the qualitatively, quantitatively studies of the expression of imprinted genes and spatially localization at the cellular level, indicating the relationship between the loss of imprinting in tissues and the stage of tumorigenesis.

The detection method of the present disclosure is different from the immunohistochemical method, reducing false positives and other negative effects. Moreover, by discovering the sites of tumor-associated imprinted genes with loss of imprinting, it is found that targeting drugs or methods leading to silencing, deletion, or rearrangement of the gene can be used to guide subsequent treatment and medication.

Example 1 Imprinted Gene Analysis for Thyroid Cancer

Figure 1:
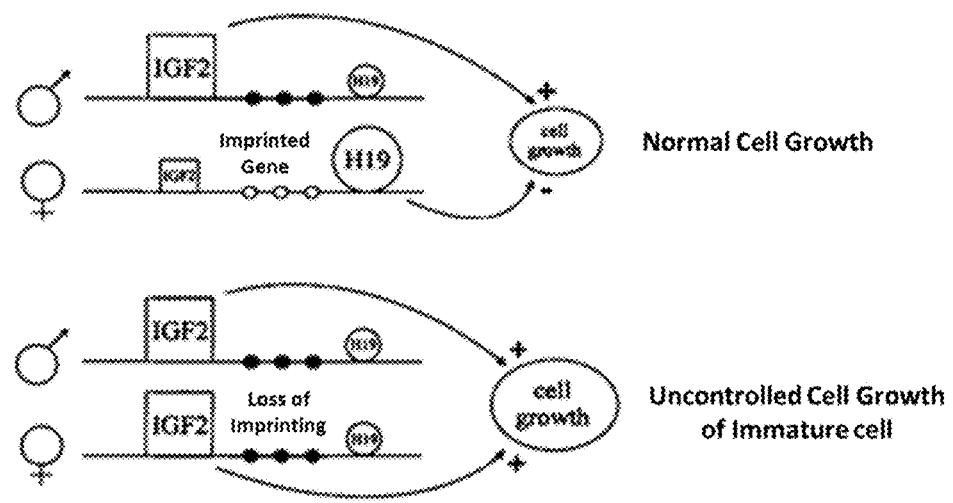
FIG. 1 is a schematic diagram showing the correlation between imprinted gene with loss of imprinting and cancer in Example 1 of the present disclosure.

This example provides a method for detecting thyroid cancer using an imprinted gene, and the correlation is as shown in FIG. 1. The method comprises the following steps:

(1) Tissue sections (10 μm) of thyroid cancer were obtained and fixed in a fixing solution described in Patent ZL200710024048.6 to prevent RNA degradation for a fixation time of 24 hours. The sections were embedded in paraffin (FFPE method) and the slides used for this experiment were positive charged slides. The sections were heated in an oven at 40° C. for more than 3 hours.

(2) The sections were dewaxed according to the sample processing method of RNASCope. The endogenous peroxidase activity in the sample was blocked, the sample was enhanced in permeability and RNA was exposed.

(3) Probe design: specific probes were designed according to the imprinted genes. The probes were designed according to imprinted genes Z1(Gnas), Z2(Igf2), Z3(Peg10), Z4(Igf2r), Z5(Mest), Z6(Plagl1), Z7(Cdkn1c), Z8(Dcn), Z9(Dlk1), Z10(Gatm), Z11(Grb10), Z12(Peg3), Z13(Sgce), Z14(Slc38a4), Z15(Diras3) and Z16(Snrpn/Snurf). Specifically, a sequence within a intron of each gene was selected for probe design. Specific probes were design by Advanced Cell Diagnostics.

(4) RNASCope in situ hybridization was performed on the samples using the probes of step (3) according to the protocol of the kit.

(5) Signal was amplified and the sections were stained with hematoxylin. The expressions of imprinted genes were analyzed through microscope images.

Figure 2:
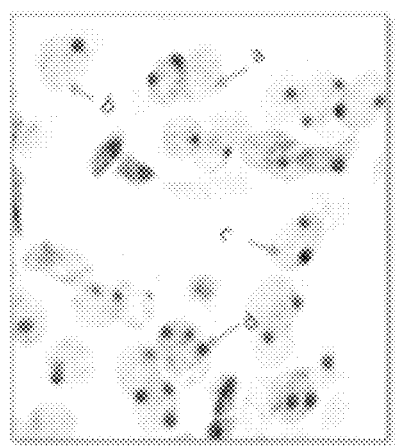
FIG. 2 shows a pathological section of thyroid cancer stained with hematoxylin for nuclei in Example 1 of the present disclosure, wherein, a represents that after performing hematoxylin staining on a cell, there is no mark in the nucleus of the cell, the imprinted gene has no expression; b represents that after performing hematoxylin staining on a cell, there is one red/brown mark in the nucleus of the cell, the imprinted gene exists; c represents that after performing hematoxylin staining on a cell, there are two red/brown marks in the nucleus of the cell, the imprinted gene loses imprinting; and d represents that after performing hematoxylin staining on a cell, there are more than two red/brown marks in the nucleus of the cell, the imprinted gene has copy number variation.
Figure 3:
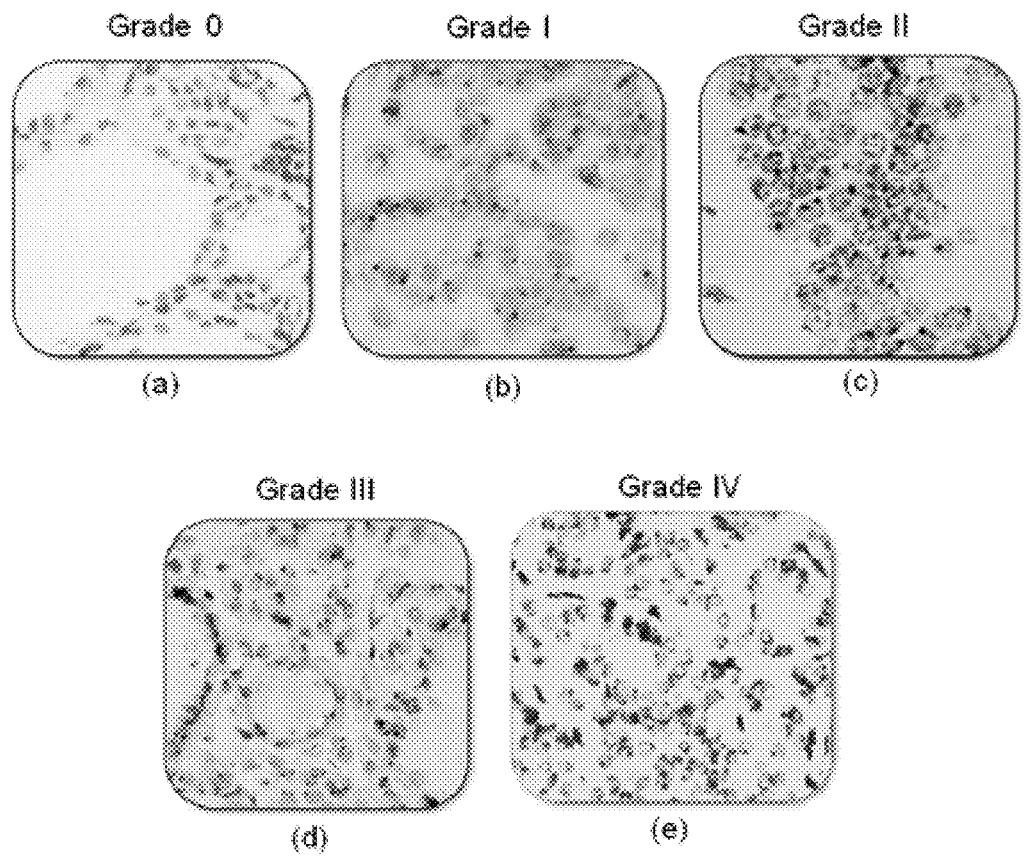
FIG. 3 shows the images of expressions of the 16 genes in pathological sections of thyroid tumors in different stages in Example 1 of the present disclosure.

In model of the present disclosure, the formulas for calculating the expression of an imprinted gene, the expression of an imprinted gene with loss of imprinting and the expression of an imprinted gene with copy number variation are as follows:

Total expression of an imprinted gene=$(b+c+d)/(a+b+c+d)\times 100\%$;

Expression of a normal imprinted gene=$b/(b+c+d)\times 100\%$;

Expression of an imprinted gene with loss of imprinting=$c/(b+c+d)\times 100\%$;

Expression of an imprinting gene with copy number variation=$d/(b+c+d)\times 100\%$;

wherein a, b, c, and d are shown in FIG. 2.

"a" represents that after performing hematoxylin staining on a cell, there is no mark in the nucleus, the imprinted gene has no expression;

"b" represents that after performing hematoxylin staining on a cell, there is one red/brown mark in the nucleus, the imprinted gene exists;

"c" represents that after performing hematoxylin staining on a cell, there are two red/brown marks in the nucleus, the imprinted gene loses imprinting; and "d" represents that after performing hematoxylin staining on a cell, there are more than two red/brown marks in the nucleus, the imprinted gene has copy number variation.

Results are shown in FIGS. 3(a)-3(e). As shown in FIGS. 3(a)-3(e), from Grade 0 to Grade IV, the proportions of cells having imprinted gene with loss of imprinting (there are two marks in one nucleus) and cells having imprinted gene with copy number variation (there are three or more marks in one nucleus) increase with the stage of malignant tumor.

Example 2 Sensitivity of Z1 to Z16 Imprinted Gene to Thyroid Cancer

Tissue sections (10 μm) of 17 patients with thyroid tumors were obtained, and the fixation and detection methods were the same as in Example 1. The results are shown in FIGS. 4(a)-4(m).

Figure 4:
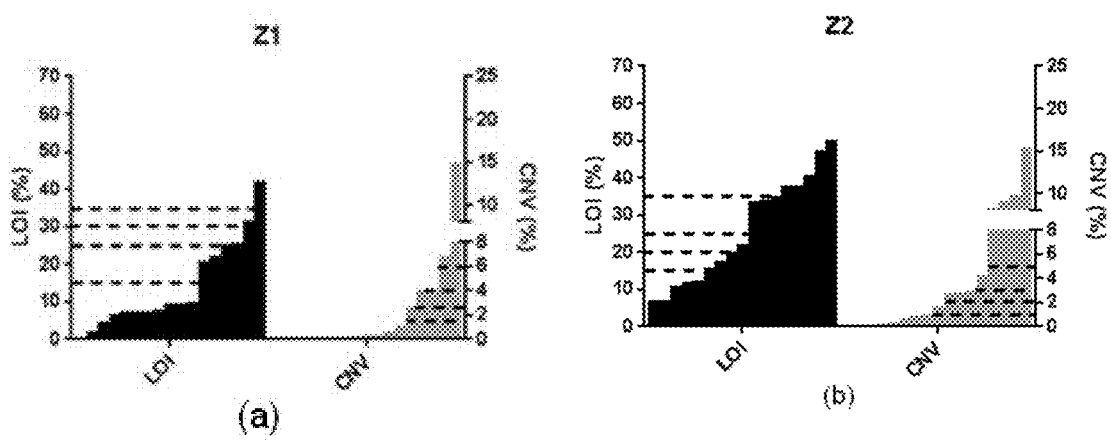
FIG. 4 shows in Example 2 of the present disclosure, the distribution ranges and grading standards of the imprinted gene with loss of imprinting and imprinted gene with copy number variation of the 16 genes in pathological sections of 17 thyroid tumors.
Figure 4:
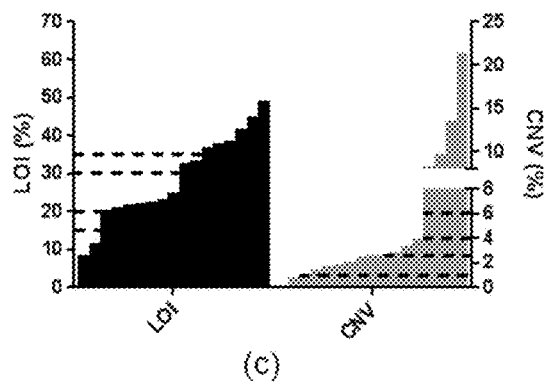
Figure 4:
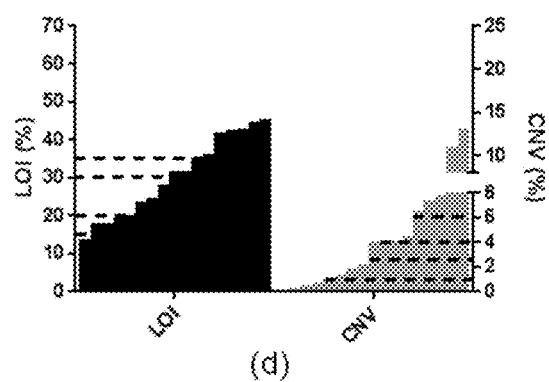
Figure 4:
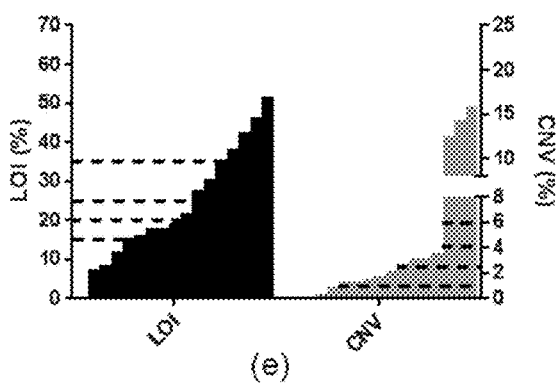
Figure 4:
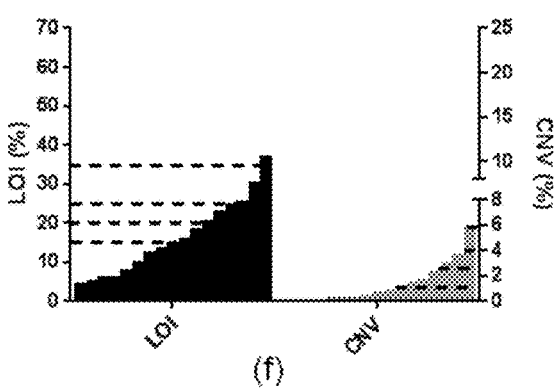
Figure 4:
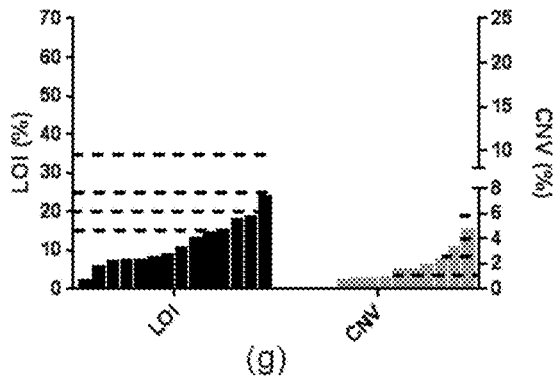
Figure 4:
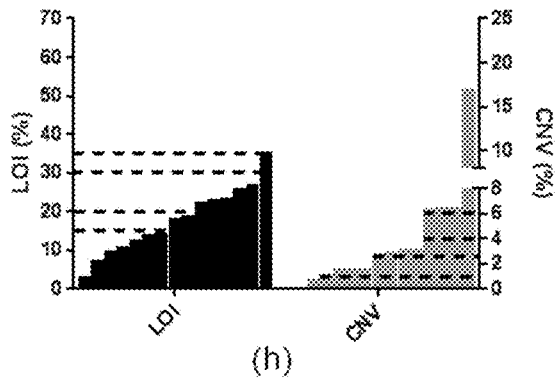
Figure 4:
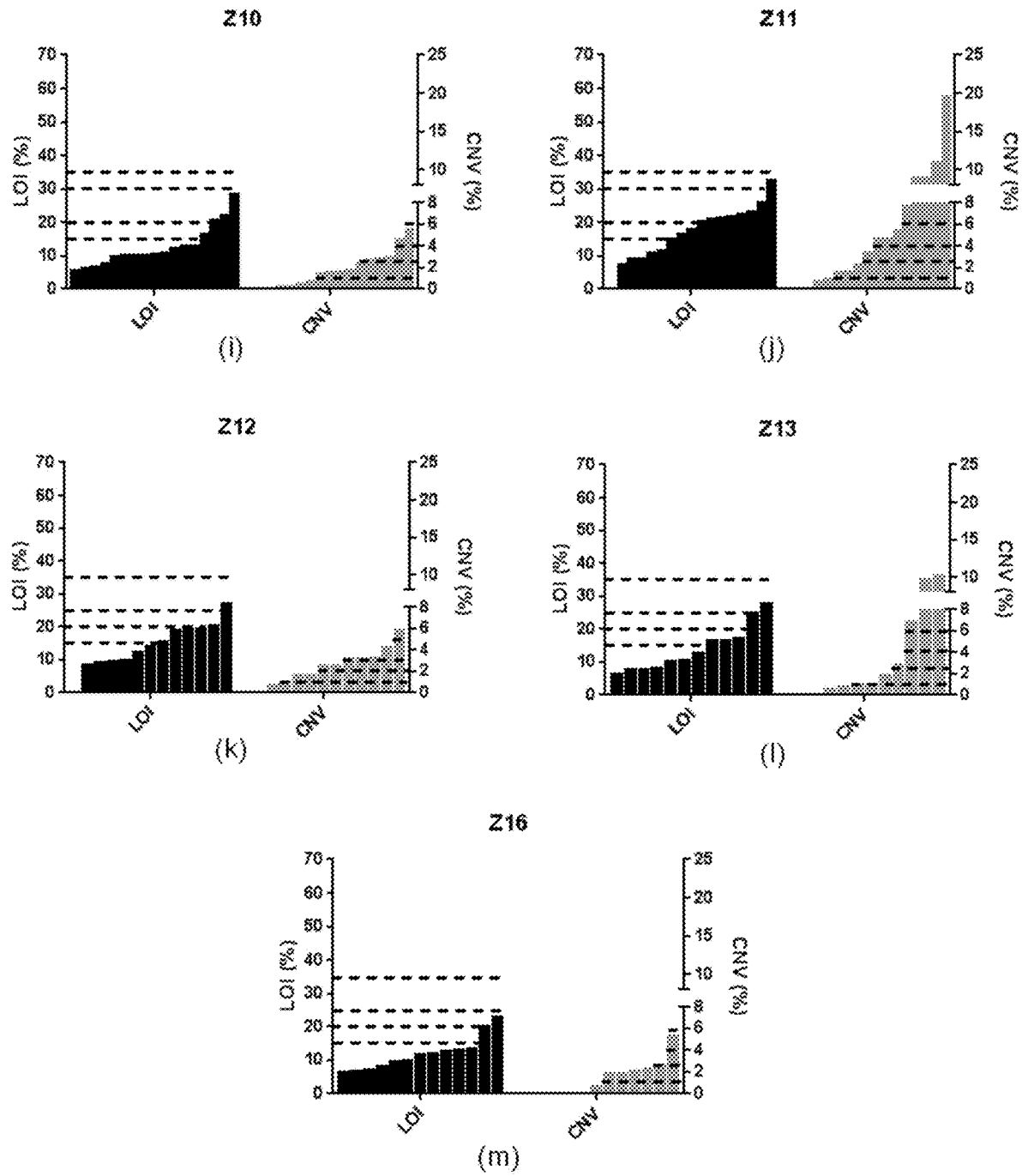

As shown in FIGS. 4(a)-4(m), the ratios of imprinted gene with loss of imprinting and imprinted gene with copy number variation of each probe in 17 thyroid tumor tissue samples showed a distribution trend from low to high. According to the distribution trend of different probes, the grading standards shown by the dotted line in the figures were calculated. The imprinted gene with loss of imprinting and the imprinted gene with copy number variation of each probe are divided into five grades from low to high, respectively, and the specific grades are classified as follows:

As shown in FIG. 4(a), for the imprinted gene Z1, Grade 0 is defined as when the expression of the imprinted gene is less than 15% and/or the expression of imprinted gene with copy number variation is less than 1.5%; Grade I is defined as when the expression of the imprinted gene is 15-25% and/or the expression of imprinted gene with copy number variation is 1.5-2.5%; Grade II is defined as when the expression of the imprinted gene is 25-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(b), for the imprinted gene Z2, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2%; Grade II is defined as when the expression of the imprinted gene is 20-25% and/or the expression of imprinted gene with copy number variation is 2-3%; Grade III is defined as when the expression of the imprinted gene is 25-35% and/or the expression of imprinted gene with copy number variation is 3-5%; and Grade IV is defined as when the expression of the imprinted gene is more than 35% and/or the expression of imprinted gene with copy number variation is more than 5%.

As shown in FIG. 4(c), for the imprinted gene Z3, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(d), for the imprinted gene Z4, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(e), for the imprinted gene Z5, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-25% and/or the expression of imprinted gene with copy number variation is 2.5-4%; Grade III is defined as when the expression of the imprinted gene is 25-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(f), for the imprinted gene Z6, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-25% and/or the expression of imprinted gene with copy number variation is 2.5-4%; Grade III is defined as when the expression of the imprinted gene is 25-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(g), for the imprinted gene Z8, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-25% and/or the expression of imprinted gene with copy number variation is 2.5-4%; Grade III is defined as when the expression of the imprinted gene is 25-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(h), for the imprinted gene Z9, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(i), for the imprinted gene Z10, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(j), for the imprinted gene Z11, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-30% and/or the expression of imprinted gene with copy number variation is 2.5-4%; Grade III is defined as when the expression of the imprinted gene is 30-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(k), for the imprinted gene Z12, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2%; Grade II is defined as when the expression of the imprinted gene is 20-25% and/or the expression of imprinted gene with copy number variation is 2-3%; Grade III is defined as when the expression of the imprinted gene is 25-35% and/or the expression of imprinted gene with copy number variation is 3-5%; and Grade IV is defined as when the expression of the imprinted gene is more than 35% and/or the expression of imprinted gene with copy number variation is more than 5%.

As shown in FIG. 4(l), for the imprinted gene Z13, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-25% and/or the expression of imprinted gene with copy number variation is 2.5-4%; Grade III is defined as when the expression of the imprinted gene is 25-35% and/or the expression of imprinted gene with copy number variation is 4-6%; and Grade IV is defined as when the expression of the imprinted gene is more than 35% and/or the expression of imprinted gene with copy number variation is more than 6%.

As shown in FIG. 4(m), for the imprinted gene Z16, Grade 0 is defined as when the expression of the imprinted gene is less than 15% and/or the expression of imprinted gene with copy number variation is less than 1%; Grade I is defined as when the expression of the imprinted gene is 15-20% and/or the expression of imprinted gene with copy number variation is 1-2.5%; Grade II is defined as when the expression of the imprinted gene is 20-25% and/or the expression of imprinted gene with copy number variation is 2.5-4%; Grade III is defined as when the expression of the imprinted gene is 25-35% and/or the expression of imprinted gene with copy number variation is 4-6%; and Grade IV is defined as when the expression of the imprinted gene is more than 35% and/or the expression of imprinted gene with copy number variation is more than 6%.

From the comprehensive analysis of these 17 thyroid tumor samples, it can be concluded that the results for determining a benign tumor or a malignant tumor in different stage are:

When the expressions of Z1, Z2, Z3, Z4, Z5, Z6, Z7, Z8, Z9, Z10, Z11, Z12, Z13, Z14, Z15 and Z16 with loss of imprinting, and the expressions of Z1, Z2, Z3, Z4, Z5, Z6, Z7, Z8, Z9, Z10, Z11, Z12, Z13, Z14, Z15 and Z16 with copy number variation are all 0 grade, no more than one of Z1, Z2, Z3, Z4, Z5, Z6, Z7, Z8, Z9, Z10, Z11, Z12, Z13, Z14, Z15 and Z16 with loss of imprinting is I grade, or no more than one of Z1, Z2, Z3, Z4, Z5, Z6, Z7, Z8, Z9, Z10, Z11, Z12, Z13, Z14, Z15 and Z16 with copy number variation is I grade, the tumor is determined as a benign tumor.

When at least two of Z1, Z2, Z3, Z4, Z5, Z6, Z7, Z8, Z9, Z10, Z11, Z12, Z13, Z14, Z15 and Z16 with loss of imprinting are I grade, or at least two of Z1, Z2, Z3, Z4, Z5, Z6, Z7, Z8, Z9, Z10, Z11, Z12, Z13, Z14, Z15 and Z16 with copy number variation are I grade; and no more than one of Z1, Z2, Z3, Z4, Z5, Z6, Z7, Z8, Z9, Z10, Z11, Z12, Z13, Z14, Z15 and Z16 with loss of imprinting is II grade, or no more than one of Z1, Z2, Z3, Z4, Z5, Z6, Z7, Z8, Z9, Z10, Z11, Z12, Z13, Z14, Z15 and Z16 with copy number variation is II grade, the tumor is determined as a malignant potential tumor.

When at least two of Z1, Z2, Z3, Z4, Z5, Z6, Z7, Z8, Z9, Z10, Z11, Z12, Z13, Z14, Z15 and Z16 with loss of imprinting are II grade, or at least two of Z1, Z2, Z3, Z4, Z5, Z6, Z7, Z8, Z9, Z10, Z11, Z12, Z13, Z14, Z15 and Z16 with copy number variation are II grade; and no more than one of Z1, Z2, Z3, Z4, Z5, Z6, Z7, Z8, Z9, Z10, Z11, Z12, Z13, Z14, Z15 and Z16 with loss of imprinting is III grade, or no more than one of Z1, Z2, Z3, Z4, Z5, Z6, Z7, Z8, Z9, Z10, Z11, Z12, Z13, Z14, Z15 and Z16 with copy number variation is III grade, the tumor is determined as an early malignant tumor.

When at least two of Z1, Z2, Z3, Z4, Z5, Z6, Z7, Z8, Z9, Z10, Z11, Z12, Z13, Z14, Z15 and Z16 with loss of imprinting are III grade, or at least two of Z1, Z2, Z3, Z4, Z5, Z6, Z7, Z8, Z9, Z10, Z11, Z12, Z13, Z14, Z15 and Z16 with copy number variation are III grade; and no more than one of Z1, Z2, Z3, Z4, Z5, Z6, Z7, Z8, Z9, Z10, Z11, Z12, Z13, Z14, Z15 and Z16 with loss of imprinting is IV grade, or no more than one of Z1, Z2, Z3, Z4, Z5, Z6, Z7, Z8, Z9, Z10, Z11, Z12, Z13, Z14, Z15 and Z16 with copy number variation is IV grade, the tumor is determined as a metaphase malignant tumor.

When at least two of Z1, Z2, Z3, Z4, Z5, Z6, Z7, Z8, Z9, Z10, Z11, Z12, Z13, Z14, Z15 and Z16 with loss of imprinting are IV grade, or at least two of Z1, Z2, Z3, Z4, Z5, Z6, Z7, Z8, Z9, Z10, Z11, Z12, Z13, Z14, Z15 and Z16 with copy number variation are IV grade, the tumor is determined as an advanced malignant tumor.

Example 3 Imprinted Gene Analysis for Skin Cancer

Tissue samples of normal black nevus and skin malignant melanoma were obtained and fixed in 10% neutral buffered formalin for more than 24 hours. Other methods were the same as in Example 1. The results are shown in FIGS. 5(a)-5(b).

Figure 5:
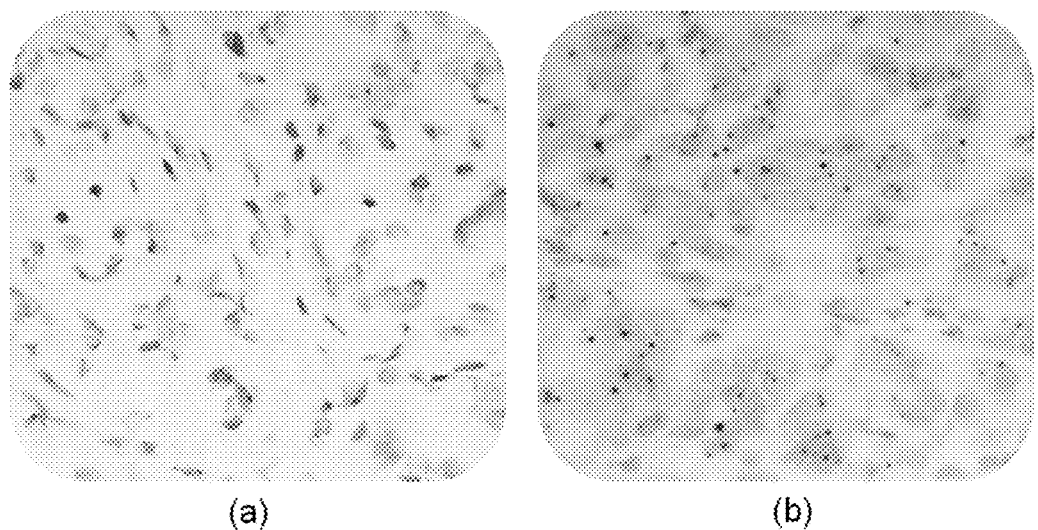
FIG. 5 shows in Example 3 of the present disclosure, the expression of the 16 genes in pathological sections of skins of different stages.

As shown in FIGS. 5(a)-5(b), FIG. 5(a) shows a benign black nevus and FIG. 5(b) shows a skin malignant melanoma. Only a few cells in the black nevus sample carried imprinted gene with loss of imprinting, and no cells were found to have imprinted gene with copy number variation, while a large number of cells in the malignant melanoma sample carried imprinted gene with loss of imprinting and imprinted gene with copy number variation.

Example 4 Imprinted Gene Analysis for Lung Cancer

Tissue samples of benign lung tumor and lung cancer were obtained and fixed in 10% neutral buffered formalin for more than 24 hours. Other methods were the same as in Example 1. The results are shown in FIGS. 6(a)-6(b).

Figure 6:
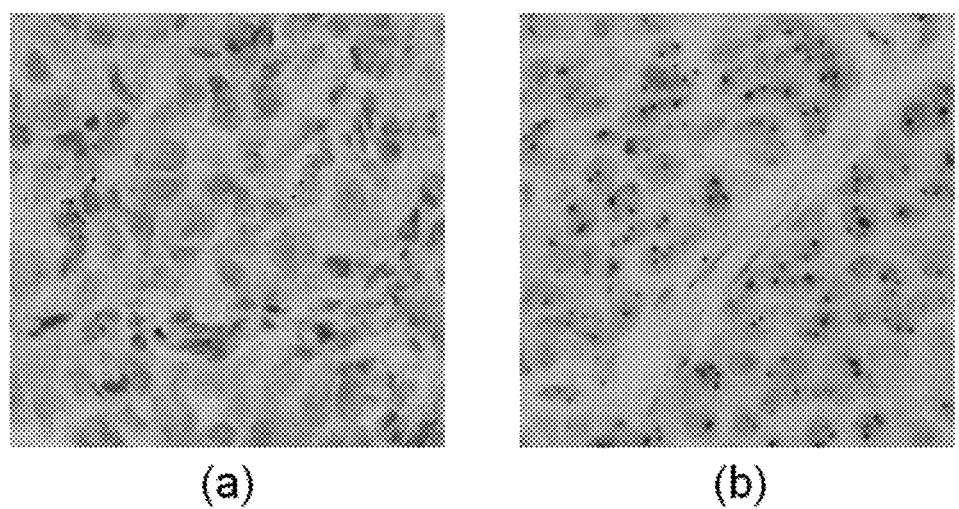
FIG. 6 shows in Example 4 of the present disclosure, the expression of the 16 genes in pathological sections of lung tumors of different stages.

As shown in FIGS. 6(a)-6(b), FIG. 6(a) shows a benign lung tumor and FIG. 6(b) shows a lung cancer. Only a few cells in the benign lung tumor sample carried imprinted gene with loss of imprinting, and no cells were found to have imprinted gene with copy number variation, while a large number of cells in the lung cancer sample carried imprinted gene with loss of imprinting and imprinted gene with copy number variation.

Example 5 Imprinted Gene Analysis for Bladder Cancer

Tissue samples of benign bladder tumor and bladder cancer were obtained and fixed in 10% neutral formalin for more than 24 hours. Other methods were the same as in Example 1. The results are shown in FIGS. 7(a)-7(b).

Figure 7:
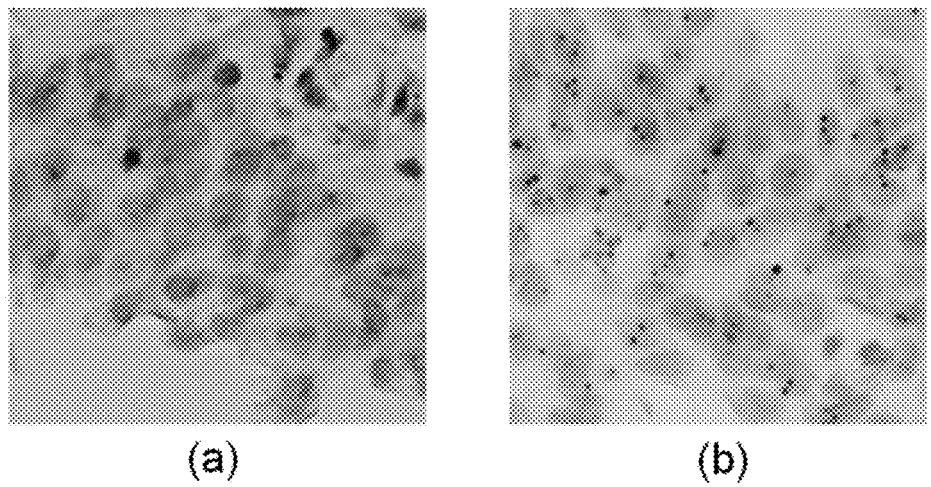
FIG. 7 shows in Example 5 of the present disclosure, the expression of the 16 genes in pathological sections of bladder tumors of different stages.

As shown in FIGS. 7(a)-7(b), FIG. 7(a) shows a benign bladder tumor and FIG. 7(b) shows a bladder cancer. Only a few cells in the benign bladder tumor sample carried imprinted gene with loss of imprinting, and no cells were found to have imprinted gene with copy number variation, while a large number of cells in the bladder cancer sample carried imprinted gene with loss of imprinting and imprinted gene with copy number variation.

Example 6 Imprinted Gene Analysis for Pancreas Cancer

Tissue samples of benign pancreas tumor and pancreas cancer were obtained and fixed in 10% neutral formalin for more than 24 hours. Other methods were the same as in Example 1. The results are shown in FIGS. 8(a)-8(b).

Figure 8:
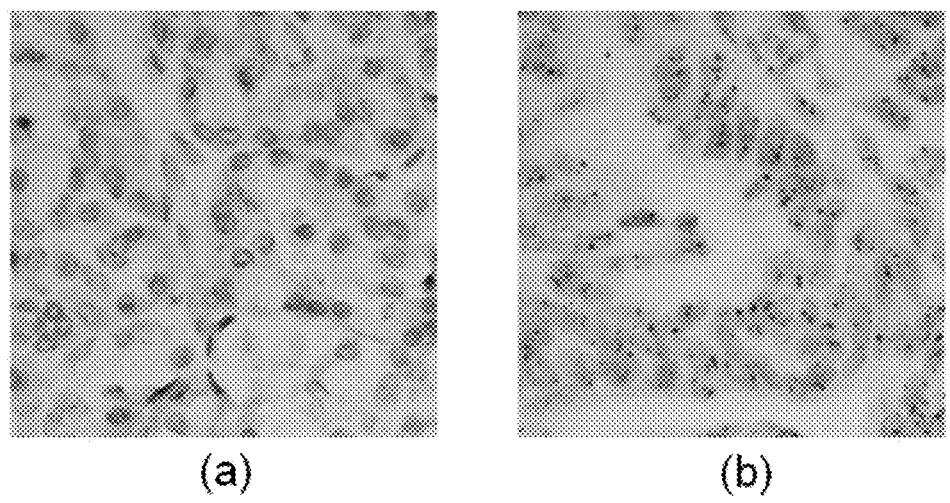
FIG. 8 shows in Example 6 of the present disclosure, the expression of the 16 genes in pathological sections of pancreas tumors of different stages.

As shown in FIGS. 8(a)-8(b), FIG. 8(a) shows a benign pancreas tumor and FIG. 8(b) shows a pancreas cancer. Only a few cells in the benign pancreas tumor sample carried imprinted gene with loss of imprinting, and no cells were found to have imprinted gene with copy number variation, while a large number of cells in the pancreas cancer sample carried imprinted gene with loss of imprinting and imprinted gene with copy number variation.

In summary, the model and device of the present disclosure present the characteristic of the imprinted gene with loss of imprinting on the tumor samples in an intuitive manner. By in situ labeling of imprinted genes, objective, intuitive, early, and accurate detection of changes in imprinted genes is achieved, and quantitative model is also provided, making a significant contribution to the diagnosis of tumors.

The Applicant declares that the present application illustrates the detailed methods of the present invention by the above examples, but not limited to the above detailed examples, that is, it does not mean that the present invention must rely on the detailed methods described above to be implemented. It should be apparent to those skilled in the art that any modifications of the present application, the equivalent replacement of each raw material of the products of the present application, the addition of an auxiliary component, the selection of a specific manner, and the like, are all within the scope of protection and disclosure of the present application.

The invention claimed is:

1. A method for determining the benignity or malignancy of a tumor in a subject and treating said subject in need of treatment, comprising
    obtaining a test sample from said subject;
    performing in situ hybridization of a probe designed based on the sequence of an intron of an imprinted gene with cells of the test sample;
    staining the test sample having been subject to the hybridization with a staining chemical and analyzing microscopic images of the stained test sample; and
    calculating the expression of the imprinted gene, the expression of the imprinted gene with loss of imprinting and the expression of the imprinted gene with copy number variation, and grading the expression of the gene with loss of imprinting and the expression of the imprinted gene with copy number variation, to determine the benignity or malignancy of a tumor and treating said subject in need of treatment by administration of medication or other treatment in accordance with the determined benignity or malignancy of said tumor;
    wherein the imprinted genes include Z1 to Z16, and wherein the imprinted gene Z1 is GNAS, the imprinted gene Z2 is IGF2, the imprinted gene Z3 is PEG10, the imprinted gene Z4 is IGF2R, the imprinted gene Z5 is MEST, the imprinted gene Z6 is PLAGL1, the imprinted gene Z7 is CDKN1C, the imprinted gene Z8 is DCN, the imprinted gene Z9 is DLK1, the imprinted gene Z10 is GATM, the imprinted gene Z11 is GRB10, the imprinted gene Z12 is PEG3, the imprinted gene Z13 is SGCE, the imprinted gene Z14 is SLC38A4, the imprinted gene Z15 is DIRAS3, and the imprinted gene Z16 is SNRPN/SNURF;
    wherein the total expression of an imprinted gene, the expression of an imprinted gene with loss of imprinting and the expression of an imprinted gene with copy number variation are calculated by the following formulas:

$$\text{Total expression of an imprinted gene} = (b+c+d)/(a+b+c+d) \times 100\%;$$

$$\text{Expression of a normal imprinted gene} = b/(b+c+d) \times 100\%;$$

$$\text{Expression of an imprinted gene with loss of imprinting} = c/(b+c+d) \times 100\%;$$

$$\text{Expression of an imprinting gene with copy number variation} = d/(b+c+d) \times 100\%;$$

wherein, a represents the number of cells each of which has no mark in the nucleus of the cell after the staining, b represents the number of cells for each of which there is one red/brown mark in the nucleus of the cell after the staining, c represents the number of cells for each of which there are two red/brown marks in the nucleus of the cell after the staining, and d represents the number of cells for each of which there are more than two red/brown markers in the nucleus of the cell after the staining.

2. The method according to claim 1, wherein the calculation of the imprinted gene expression comprises calculating the expression of two or more imprinted genes from Z1 to Z16.

3. The method according to claim 1, wherein the staining chemical is hematoxylin.

4. The method according to claim 1, wherein the total expression of an imprinted gene, the expression of an imprinted gene with loss of imprinting and the expression of an imprinted gene with copy number variation are classified into 5 grades.

5. The method according to claim 4, wherein the 5 grades are classified respectively according to the total expression of an imprinted gene, the expression of an imprinted gene with loss of imprinting and the expression of an imprinted gene with copy number variation of the 16 imprinted genes Z1 to Z16.

6. The method according to claim 4, wherein the expression of Z1 with loss of imprinting and the expression of Z1 with copy number variation are classified into 5 grades:
    Grade 0: the expression of Z1 with loss of imprinting is less than 15% and/or the expression of Z1 with copy number variation is less than 1.5%;
    Grade I: the expression of Z1 with loss of imprinting is 15-25% and/or the expression of Z1 with copy number variation is 1.5-2.5%;
    Grade II: the expression of Z1 with loss of imprinting is 25-30% and/or the expression of Z1 with copy number variation is 2.5-4%;
    Grade III: the expression of Z1 with loss of imprinting is 30-35% and/or the expression of Z1 with copy number variation is 4-6%; and
    Grade IV: the expression of Z1 with loss of imprinting is more than 35% and/or the expression of Z1 with copy number variation is more than 6%.

7. The method according to claim 6, wherein the expression of each of Z2 and Z12 with loss of imprinting and the expression of each of Z2 and Z12 with copy number variation are classified into 5 grades:
    Grade 0: the expression of Z2 or Z12 with loss of imprinting is less than 15% and/or the expression of Z2 or Z12 with copy number variation is less than 1%;
    Grade I: the expression of Z2 or Z12 with loss of imprinting is 15-20% and/or the expression of Z2 or Z12 with copy number variation is 1-2%;
    Grade II: the expression of Z2 or Z12 with loss of imprinting is 20-25% and/or the expression of Z2 or Z12 with copy number variation is 2-3%;

Grade III: the expression of Z2 or Z12 with loss of imprinting is 25-35% and/or the expression of Z2 or Z12 with copy number variation is 3-5%; and Grade IV: the expression of Z2 or Z12 with loss of imprinting is more than 35% and/or the expression of Z2 or Z12 with copy number variation is more than 5%.

8. The method according to claim 7, wherein the expression of each of Z3, Z4, Z9, Z10 or Z11 with loss of imprinting and the expression of each of Z3, Z4, Z9, Z10 or Z11 with copy number variation are classified into 5 grades:

Grade 0: the expression of any of Z3, Z4, Z9, Z10 or Z11 with loss of imprinting is less than 15% and/or the expression of any of Z3, Z4, Z9, Z10 or Z11 with copy number variation is less than 1%;

Grade I: the expression of any of Z3, Z4, Z9, Z10 or Z11 with loss of imprinting is 15-20% and/or the expression of any of Z3, Z4, Z9, Z10 or Z11 with copy number variation is 1-2.5%;

Grade II: the expression of any of Z3, Z4, Z9, Z10 or Z11 with loss of imprinting is 20-30% and/or the expression of any of Z3, Z4, Z9, Z10 or Z11 with copy number variation is 2.5-4%;

Grade III: the expression of any of Z3, Z4, Z9, Z10 or Z11 with loss of imprinting is 30-35% and/or the expression of any of Z3, Z4, Z9, Z10 or Z11 with copy number variation is 4-6%; and Grade IV: the expression of any of Z3, Z4, Z9, Z10 or Z11 with loss of imprinting is more than 35% and/or the expression of any of Z3, Z4, Z9, Z10 or Z11 with copy number variation is more than 6%.

9. The method according to claim 8, wherein the expression of each of Z5, Z6, Z8, Z13 or Z16 with loss of imprinting and the expression of each of Z5, Z6, Z8, Z13 or Z16 with copy number variation are classified into 5 grades:

Grade 0: the expression of any of Z5, Z6, Z8, Z13 or Z16 with loss of imprinting is less than 15% and/or the expression of any of Z5, Z6, Z8, Z13 or Z16 with copy number variation is less than 1%;

Grade I: the expression of any of Z5, Z6, Z8, Z13 or Z16 with loss of imprinting is 15-20% and/or the expression of any of Z5, Z6, Z8, Z13 or Z16 with copy number variation is 1-2.5%;

Grade II: the expression of any of Z5, Z6, Z8, Z13 or Z16 with loss of imprinting is 20-25% and/or the expression of any of Z5, Z6, Z8, Z13 or Z16 with copy number variation is 2.5-4%;

Grade III: the expression of any of Z5, Z6, Z8, Z13 or Z16 with loss of imprinting is 25-35% and/or the expression of any of Z5, Z6, Z8, Z13 or Z16 with copy number variation is 4-6%; and Grade IV: the expression of any of Z5, Z6, Z8, Z13 or Z16 with loss of imprinting is more than 35% and/or the expression of any of Z5, Z6, Z8, Z13 or Z16 with copy number variation is more than 6%.

10. The method according to claim 9, wherein the expression of each of Z7, Z14 or Z15 with loss of imprinting and the expression of each of Z7, Z14 or Z15 with copy number variation are classified into 5 grades:

Grade 0: the expression of any of Z7, Z14 or Z15 with loss of imprinting is less than 10% and/or the expression of any of Z7, Z14 or Z15 with copy number variation is less than 0.5%;

Grade I: the expression of any of Z7, Z14 or Z15 with loss of imprinting is 10-15% and/or the expression of any of Z7, Z14 or Z15 with copy number variation is 0.5-1%;

Grade II: the expression of any of Z7, Z14 or Z15 with loss of imprinting is 15-20% and/or the expression of any of Z7, Z14 or Z15 with copy number variation is 1-2%;

Grade III: the expression of any of Z7, Z14 or Z15 with loss of imprinting is 20-25% and/or the expression of any of Z7, Z14 or Z15 with copy number variation is 2-3%; and Grade IV: the expression of any of Z7, Z14 or Z15 with loss of imprinting is more than 25% and/or the expression of any of Z7, Z14 or Z15 with copy number variation is more than 3%.

11. The method according to claim 10, wherein the benignity or malignancy of the tumor to be determined is classified as benign tumor, malignant potential tumor, early malignant tumor, moderate malignant tumor, or advanced malignant tumor.

12. The method according to claim 11, wherein the tumor is determined as a benign tumor, if the expression of all the imprinted genes Z1, Z2, Z3, Z4, Z5, Z6, Z7, Z8, Z9, Z10, Z11, Z12, Z13, Z14, Z15 and Z16 with loss of imprinting and the expression of all the imprinted genes Z1, Z2, Z3, Z4, Z5, Z6, Z7, Z8, Z9, Z10, Z11, Z12, Z13, Z14, Z15 and Z16 with copy number variation is Grade 0, if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade I or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade I.

13. The method according to claim 11, wherein the tumor is determined as a malignant potential tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade I, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade I, and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade II.

14. The method according to claim 11, wherein the tumor is determined as an early malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade II, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade II, and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade III, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade III.

15. The method according to claim 11, wherein the tumor is determined as a moderate malignant tumor, if the expression of at least two of the imprinted genes Z1Z2, Z3, Z4, Z5, Z6, Z7, Z8, Z9, Z10, Z11, Z12, Z13, Z14, Z15 and Z16 with loss of imprinting is Grade III, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade III, and if the expression of no more than one of the imprinted genes Z1, Z2, Z3, Z4, Z5, Z6, Z7, Z8, Z9, Z10, Z11, Z12, Z13, Z14, Z15 and Z16 with loss of imprinting is Grade IV, or if the expression of no more than one of the imprinted genes Z1, Z2, Z3, Z4, Z5, Z6, Z7, Z8, Z9, Z10, Z11, Z12, Z13, Z14, Z15 and Z16 with copy number variation is Grade IV.

16. The method according to claim 11, wherein the tumor is determined as an advanced malignant tumor, if the expression of at least two of the imprinted genes Z1, Z2, Z3, Z4, Z5, Z6, Z7, Z8, Z9, Z10, Z11, Z12, Z13, Z14, Z15 and Z16 with loss of imprinting is Grade IV, or if the expression of at least two of the imprinted genes Z1, Z2, Z3, Z4, Z5, Z6, Z7, Z8, Z9, Z10, Z11, Z12, Z13, Z14, Z15 and Z16 with copy number variation is Grade IV.

17. The method according to claim 1, wherein the test sample is human tissue and/or cells.

18. The method according to claim 1, wherein the test sample is needle biopsy sample.

19. The method according to claim 1, wherein the in situ hybridization is RNAscope in situ hybridization.

20. The method according to claim 19, wherein the RNAscope in situ hybridization is performed by using singleplex or multiplex color assay kit or singleplex or multiplex fluorescence assay kit.

* * * * *